(12) United States Patent
Morishita

(10) Patent No.: US 11,232,584 B2
(45) Date of Patent: *Jan. 25, 2022

(54) LINE-OF-SIGHT ESTIMATION DEVICE, LINE-OF-SIGHT ESTIMATION METHOD, AND PROGRAM RECORDING MEDIUM

(71) Applicant: NEC CORPORATION, Tokyo (JP)

(72) Inventor: Yusuke Morishita, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/346,006

(22) PCT Filed: Oct. 31, 2016

(86) PCT No.: PCT/JP2016/082282
§ 371 (c)(1),
(2) Date: Apr. 29, 2019

(87) PCT Pub. No.: WO2018/078857
PCT Pub. Date: May 3, 2018

(65) Prior Publication Data
US 2020/0058136 A1 Feb. 20, 2020

(51) Int. Cl.
*G06K 9/00* (2006.01)
*G06T 7/73* (2017.01)
(Continued)

(52) U.S. Cl.
CPC ............... *G06T 7/73* (2017.01); *G06F 3/013* (2013.01); *G06K 9/00248* (2013.01);
(Continued)

(58) Field of Classification Search
CPC .......................... G06F 3/013; G06K 9/00248; G06K 9/00255; G06K 9/00604;
(Continued)

(56) References Cited

U.S. PATENT DOCUMENTS 10,846,877 B2 * 11/2020 Lagun ................. G06K 9/6228
2012/0189160 A1 * 7/2012 Kaneda ................. A61B 3/113
382/103
(Continued)

FOREIGN PATENT DOCUMENTS

CN  109492514  * 3/2019  ......... G06K 9/00604
JP  2003-256804 A  9/2003
(Continued)

OTHER PUBLICATIONS

Jian-Gang Wang, et al., "Eye Gaze Estimation from a Single Image of One Eye", Proc. IEEE ICCV, 2003, pp. I-136-143.
(Continued)

*Primary Examiner* — Amara Abdi
(74) *Attorney, Agent, or Firm* — Sughrue Mion, PLLC

(57) ABSTRACT

The purpose of the present invention is to improve the accuracy of line-of-sight estimation based on an image. A line-of-sight estimation device 100 comprises: an estimation unit 110 which estimates lines of sight from a face included in a face image, using a plurality of estimators; and a determination unit 120 which determines a line of sight for the face on the basis of first condition information including conditions relating to the capture of the face image, and a plurality of sets of second condition information, each including conditions associated with one of the plurality of estimators, and on the basis of a plurality of estimated lines of sight.

8 Claims, 7 Drawing Sheets

(51) Int. Cl.
*G06T 7/77* (2017.01)
*G06F 3/01* (2006.01)

(52) U.S. Cl.
CPC ..... *G06K 9/00255* (2013.01); *G06K 9/00604* (2013.01); *G06T 7/77* (2017.01); *G06T 2207/20072* (2013.01); *G06T 2207/20081* (2013.01); *G06T 2207/30201* (2013.01)

(58) Field of Classification Search
CPC . G06T 2207/20072; G06T 2207/20081; G06T 2207/30201; G06T 7/73; G06T 7/77; G06T 7/70; G06T 1/00; A61B 3/113
See application file for complete search history.

(56) References Cited

U.S. PATENT DOCUMENTS

| | | | | |
|---|---|---|---|---|
| 2014/0016871 | A1* | 1/2014 | Son | G06T 11/60 382/201 |
| 2015/0003819 | A1* | 1/2015 | Ackerman | H04N 5/23219 396/51 |
| 2017/0255817 | A1 | 9/2017 | Tomimori et al. | |
| 2019/0188878 | A1 | 6/2019 | Matsuura | |
| 2020/0213575 | A1 | 7/2020 | Shibagami et al. | |
| 2020/0250403 | A1 | 8/2020 | Xiao et al. | |
| 2020/0275062 | A1 | 8/2020 | Yamamoto et al. | |

FOREIGN PATENT DOCUMENTS

| | | | | |
|---|---|---|---|---|
| JP | 2003256804 | * | 9/2003 | ............... G06T 1/00 |
| JP | 2009-059257 | A | 3/2009 | |
| JP | 4829141 | B2 | 12/2011 | |
| JP | 2012-037934 | A | 2/2012 | |
| JP | 2003256804 | * | 9/2012 | ............ H04N 5/225 |
| JP | 5238880 | B2 | 7/2013 | |
| JP | 2015-022700 | A | 2/2015 | |
| JP | 5772821 | B2 | 9/2015 | |

OTHER PUBLICATIONS

Xucong Zhang, et al., "Appearance-Based Gaze Estimation in the Wild", Proc. IEEE CVPR, 2015, pp. 4511-4520.
International Search Report for PCT/JP2016/082282 dated Jan. 24, 2017 [PCT/ISA/210].
Japanese Office Action for JP Application No. 2018-547082 dated Dec. 8, 2020 with English Translation.
US Office Action and PTO-892 for U.S. Appl. No. 16/670,202 dated Mar. 11, 2021.
US Office Action for U.S. Appl. No. 16/670,254 dated Mar. 15, 2021.

* cited by examiner

LINE-OF-SIGHT ESTIMATION DEVICE, LINE-OF-SIGHT ESTIMATION METHOD, AND PROGRAM RECORDING MEDIUM

CROSS REFERENCE TO RELATED APPLICATIONS

This application is a National Stage of International Application No. PCT/JP2016/082282 filed Oct. 31, 2016.

TECHNICAL FIELD

The present disclosure relates to a gaze estimation device and the like.

BACKGROUND ART

A gaze (an orientation of an eye) of a human can be an important clue to analyze action or intention of a person. Thus, a technique for estimating information relating to a gaze of a human, particularly, a technique for estimating a gaze, based on an image (hereinafter, also referred to as a "face image") including a face of a human is widely studied.

As techniques for estimating a gaze, based on a face image, there are, for example, techniques described in PTLs 1 to 3, and NPLs 1 to 2. PTL 1 discloses one example of feature-based methods using a feature (image feature) included in an image. Further, PTL 2 and NPL 2 each disclose one example of appearance-based methods utilizing appearance of an object. NPL 1 discloses a method of estimating a gaze by approximating a shape of an iris of a pupil with an ellipse.

CITATION LIST

Patent Literature

[PTL 1] Japanese Patent No. 4829141
[PTL 2] Japanese Unexamined Patent Application Publication No. 2009-059257
[PTL 3] Japanese Patent No. 5772821

Non Patent Literature

[NPL 1] J. Wang, E. Sung, and R. Venkateswarlu, "Eye Gaze Estimation from a Single Image of One Eye," Proc. IEEE ICCV 2003, pp. I-136-143, 2003.
[NPL 2] X. Zhang, Y. Sugano, M. Fritz and A. Bulling, "Appearance-Based Gaze Estimation in the Wild," Proc. IEEE CVPR 2015, pp. 4511-4520, 2015.

SUMMARY OF INVENTION

Technical Problem

As described above, various methods are used for gaze estimation, and each have a characteristic. However, each of the methods has a possibility of deteriorating in accuracy of estimation, when an orientation of a face, brightness of illumination, and the like are under a particular condition.

An exemplary object of the present disclosure is to provide a technique for improving accuracy of gaze estimation based on an image.

Solution to Problem

In one aspect, there is provided a gaze estimation device, including: an estimation means for estimating a gaze of a face included in a face image with a plurality of estimators; and a determination means for determining a gaze of the face, based on first condition information including a condition relating to capture of the face image, a plurality of pieces of second condition information each including the condition associated with one of the plurality of estimators, and the estimated plurality of gazes.

In another aspect, there is provided a gaze estimation method, including: estimating a gaze of a face included in a face image with a plurality of estimators; and determining a gaze of the face, based on first condition information including a condition relating to capture of the face image, a plurality of pieces of second condition information each including the condition associated with one of the plurality of estimators, and the estimated plurality of gazes.

In still another aspect, there is provided a computer-readable program recording medium recording a program which causes a computer to execute: processing of estimating a gaze of a face included in a face image with a plurality of estimators; and processing of determining a gaze of the face, based on first condition information including a condition relating to capture of the face image, a plurality of pieces of second condition information each including the condition associated with one of the plurality of estimators, and the estimated plurality of gazes.

Advantageous Effects of Invention

According to the present disclosure, accuracy of gaze estimation based on an image is improved.

EXAMPLE EMBODIMENT

First Example Embodiment

Figure 1:
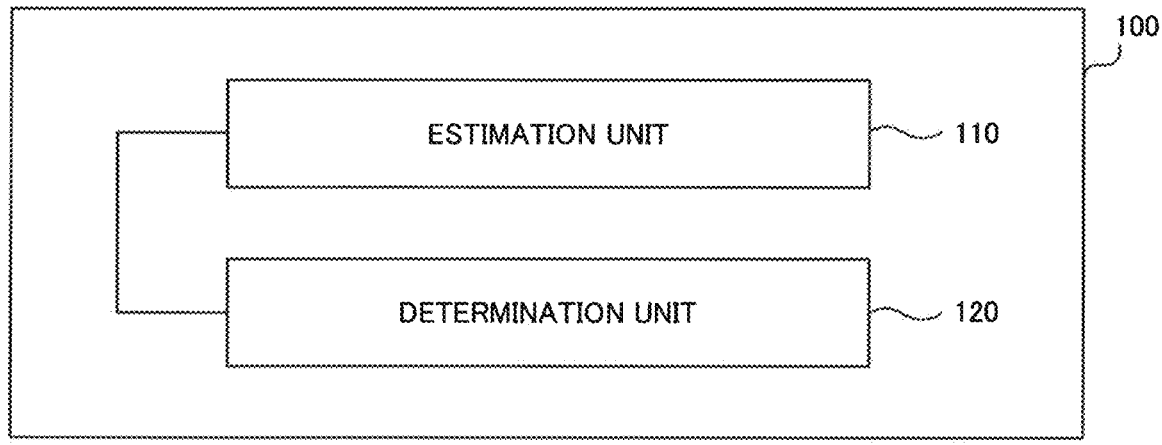
FIG. 1 is a block diagram illustrating one example of a configuration of a gaze estimation device.

FIG. 1 is a block diagram illustrating a configuration of a gaze estimation device 100 according to one example embodiment. The gaze estimation device 100 is a device serving to estimate a gaze included in a face image. The gaze estimation device 100 includes at least an estimation unit 110 and a determination unit 120. However, the gaze estimation device 100 may include another component as necessary.

Herein, a face image refers to an image including a part or all of a face of a human. A face image is an image captured by an imaging device (a surveillance camera, an internal camera of an electronic instrument, or the like). A face image may be such a captured image itself, or a part of a captured image, i.e., an image in which a region equivalent to a face is extracted from a captured image.

The estimation unit 110 estimates a gaze of a face included in a face image. For example, by estimating a region of an eye included in a face image, the estimation unit 110 estimates a gaze, i.e., a direction (more accurately, an orientation) in which an eye of a human is seeing. An estimation method of a gaze by the estimation unit 110 may be any known method. For example, the estimation unit 110 can estimate a gaze by using machine learning such as supervised learning. Specifically, the estimation unit 110 may learn a relation between a face image and a gaze by use of a previously collected face image.

The estimation unit 110 estimates a gaze of a face included in a face image by a plurality of estimators. In other words, the estimation unit 110 estimates a gaze by use of a plurality of estimation methods, for a single face image. A gaze estimated by a plurality of estimators can differ in its direction. Therefore, there are a plurality of patterns of gazes estimated by the estimation unit 110.

A plurality of estimators each estimate a gaze of a face included in a face image, based on a predetermined algorithm. A plurality of estimators may be each achieved by a different circuitry, but may be achieved by a single circuitry. A plurality of estimators may be achieved by use of software.

When gaze estimation is performed by machine learning, a difference of estimators can be made by a difference of data used for advance learning. In other words, the estimation unit 110 may estimate a gaze, based on each of learning using a certain data set and learning using another data set. When a data set used for advance learning differs, an estimation result of a gaze based on the data set can also differ.

The determination unit 120 determines a gaze of a face included in a face image. Specifically, the determination unit 120 determines a gaze, based on an estimation result of a gaze by the estimation unit 110. In other words, the determination unit 120 determines a single direction, based on a plurality of gazes (i.e., a plurality of directions) estimated by the estimation unit 110.

More specifically, the determination unit 120 determines a gaze, based on a plurality of gazes estimated by the estimation unit 110, first condition information, and second condition information. The first condition information includes at least a condition relating to capture of a face image. In other words, the first condition information includes information indicating how a face image is captured by an imaging device. The first condition information may represent such a condition by a numerical value representing a physical quantity or the like.

As one example, the first condition information may be information indicating a relative position relation between an imaging device and a person being a subject. Specifically, the first condition information may indicate a distance between an imaging device and a person, or height of an imaging device referenced to height of a face of a person. Alternatively, the first condition information may be information indicating performance of an imaging device. Specifically, the first condition information may indicate a parameter (a field angle or the like) of an optical system of an imaging device.

Furthermore, the first condition information may indicate an installation angle of an imaging device. Herein, an installation angle of an imaging device refers to an angle formed by a direction of a face of a person to be captured, and an optical axis direction of an imaging device. A direction of a face referred to herein may be calculated based on a face image, or may be previously determined. For example, when an unspecified number of persons passing along a certain passage are captured by an imaging device, a direction of a face may be an average or typical direction of a face of a person passing along the passage. In this case, there is a high possibility that a direction of a face coincides with a traveling direction of a passage. Note that an installation angle may be represented by a horizontal angle and an elevation/depression angle (also referred to as a vertical angle.), or may be represented by only a horizontal angle with a vertical angle omitted.

On the other hand, the second condition information includes at least a condition associated with each of a plurality of estimators of the estimation unit 110. A condition represented by the second condition information is comparable with a condition represented by the first condition information. For example, in a case where a gaze is estimated based on machine learning based on a data set of a face image collected in advance, a condition represented by the second condition information may be a distance between an imaging device and a person when a face image included in the data set is captured, or an installation angle or a field angle (or an average value of one of these angles) of an imaging device.

The determination unit 120 can determine a gaze by comparing the first condition information with the second condition information. For example, the determination unit 120 compares a condition when a face image is captured, with a plurality of conditions (in other words, a plurality of conditions associated with a plurality of estimators used for estimation of a plurality of gazes) associated with a plurality of gazes estimated by the estimation unit 110. The determination unit 120 determines a gaze, based on these comparison results.

Specifically, the determination unit 120 determines a gaze in such a way that a condition represented by the second condition information becomes closer to a gaze being closer to a condition represented by the first condition information, among a plurality of gazes estimated by the estimation unit 110. For example, the determination unit 120 may determine a gaze by executing weighted calculation (weighted addition, weighted average, or the like) in which weight dependent on a result of comparison between the first condition information and the second condition information is given to a plurality of gazes estimated by the estimation unit 110. Note that the determination unit 120 may compare the first condition information with the second condition information, and execute the above-described weighted calculation after excluding an estimation result that does not satisfy a certain criterion.

Figure 2:
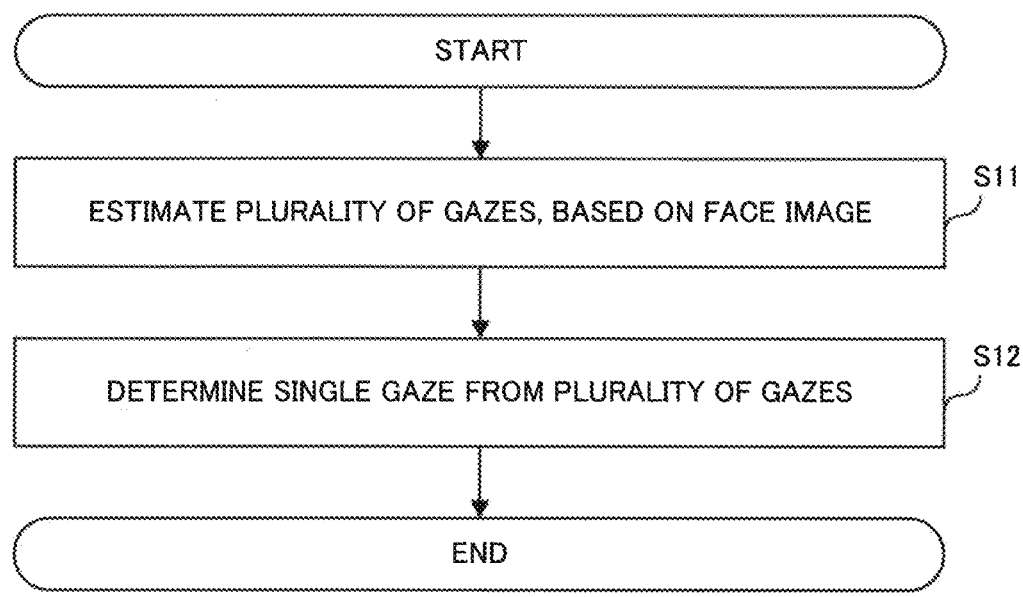
FIG. 2 is a flowchart illustrating one example of a gaze estimation method.

FIG. 2 is a flowchart illustrating a gaze estimation method according to the present example embodiment. By executing processing in accordance with this flowchart, the gaze estimation device 100 can estimate a gaze of a face included in a face image.

In a step S11, the estimation unit 110 estimates a plurality of gazes, based on a face image. More specifically, the estimation unit 110 calculates a plurality of gazes as estimation results, by applying a plurality of estimators to one face image. In other words, it can also be said that the estimation unit 110 estimates a gaze by a plurality of methods.

In a step S12, the determination unit 120 determines a single gaze, based on a plurality of gazes estimated in the step S11. More specifically, the determination unit 120 determines a gaze associated with a face image used for the estimation in the step S11, based on the first condition information and the second condition information.

As described above, the gaze estimation device 100 according to the present example embodiment has a configuration which estimates a gaze of a face included in a face image by a plurality of estimators, and determines a single gaze, based on the estimated plurality of gazes. This configuration can reduce a possibility that accuracy of estimation deteriorates, as compared with a case where a gaze is estimated by use of a single estimator. Therefore, according to the gaze estimation device 100, it is possible to improve accuracy of gaze estimation.

Accuracy of gaze estimation can fluctuate due to various factors. For example, accuracy of gaze estimation can fluctuate due to a condition relating to capture of a face image. Specifically, accuracy of gaze estimation can fluctuate due to a relative position relation (an orientation of a face, or the like) between a person being a subject and an imaging device. Moreover, accuracy of gaze estimation can also fluctuate due to performance of an imaging device itself, a condition of illumination such as brightness, or the like. In addition, there is a possibility that accuracy of gaze estimation can deteriorate under a particular condition depending on a method of the estimation.

The gaze estimation device 100 can suppress deterioration of accuracy resulting from use of a single estimator, by determining a gaze, based on a plurality of gazes estimated by use of a plurality of estimators. Therefore, according to the gaze estimation device 100, it is possible to obtain an estimation result robust against a condition under which a face image is captured. In other words, the gaze estimation device 100 can achieve a favorable gaze estimation for face images captured under various conditions.

Second Example Embodiment

Figure 3:
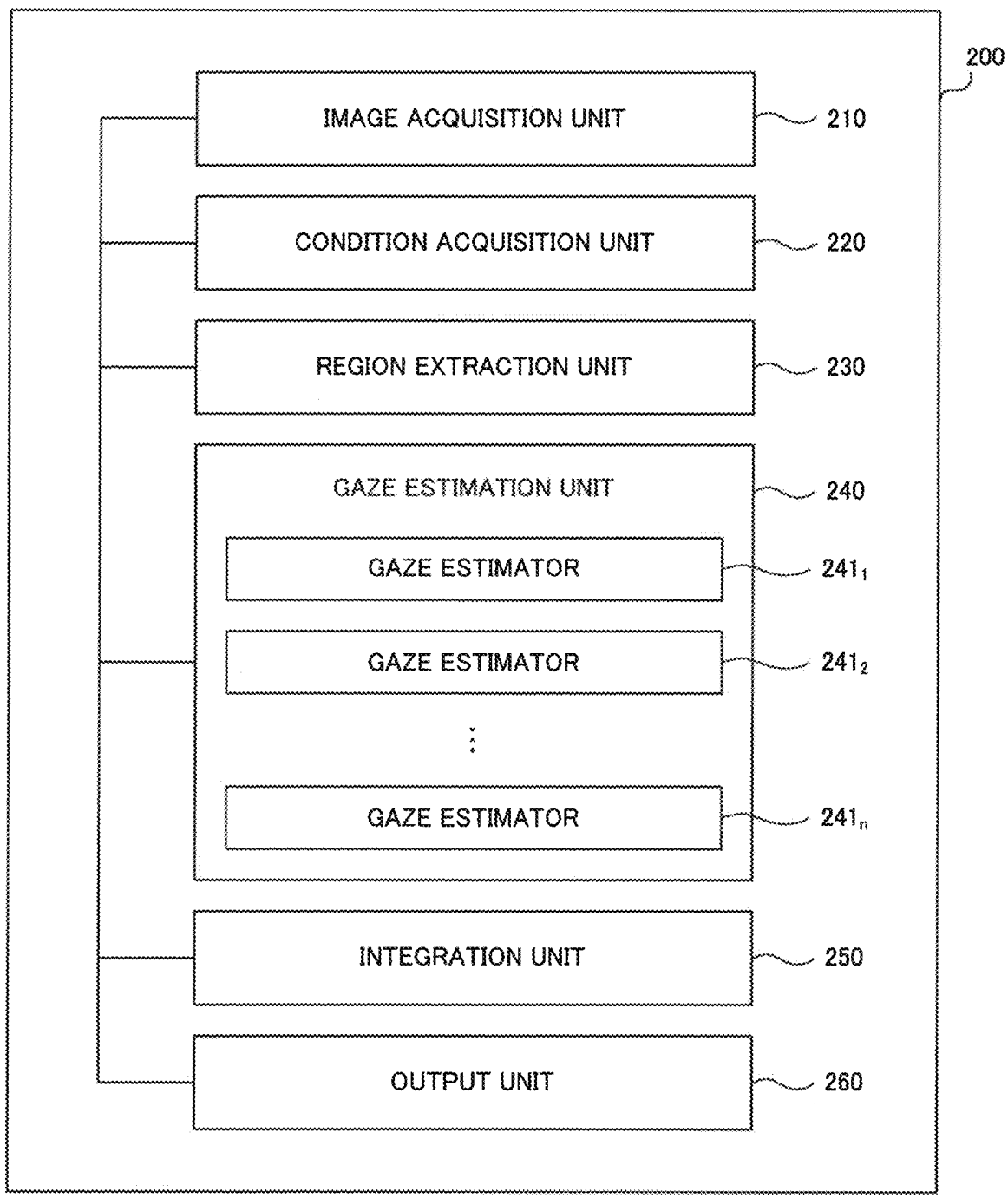
FIG. 3 is a block diagram illustrating one example of a configuration of a data processing device.

FIG. 3 is a block diagram illustrating a configuration of a data processing device 200 according to another example embodiment. The data processing device 200 is equivalent to one example of the gaze estimation device 100 according to the first example embodiment. The data processing device 200 includes an image acquisition unit 210, a condition acquisition unit 220, a region extraction unit 230, a gaze estimation unit 240, an integration unit 250, and an output unit 260.

The data processing device 200 is a device serving to estimate a gaze, based on an image. An image referred to herein may be either a still image or a moving image. For example, when a gaze is estimated based on a moving image, there is a possibility that a face image is included in a certain period of the moving image, and a face image is not included in another period. In such a case, the data processing device 200 may be configured in such a way as to estimate a gaze for an image in a period when a face image is included, and not to estimate a gaze (not to output an estimation result) for an image in a period when a face image is not included.

The image acquisition unit 210 acquires an image. For example, the image acquisition unit 210 acquires an image by receiving image data from another device. Another device referred to herein may be an imaging device such as a surveillance camera, or a storage device such as a database recording a plurality of pieces of image data. The image acquisition unit 210 supplies image data to the region extraction unit 230.

Image data referred to herein are data in which an image is expressed by luminance values of a plurality of pixels. A number of pixels, a number of colors (a number of color components), a number of gradations, and the like in image data are not limited to particular numerical values. For image data acquired by the image acquisition unit 210, a number of pixels and a number of colors may be previously determined, but may not necessarily be so. For convenience of description, hereinafter, image data acquired by the image acquisition unit 210 are also referred to as "input image data".

For convenience of description, hereinafter, it is assumed that one piece of image data can include only one face image, and does not include a plurality of face images. However, when one piece of image data includes a plurality of face images, the data processing device 200 has only to execute later-described processing for each of the plurality of face images.

The image acquisition unit 210 may supply input image data to the region extraction unit 230 as it is, but may supply input image data to the region extraction unit 230 after processing the image data. For example, by detecting a face of a human from an image represented by image data, the image acquisition unit 210 may generate image data representing a face image being a part of the image, and supply the generated image data to the region extraction unit 230.

Alternatively, the image acquisition unit 210 may supply image data to the region extraction unit 230 after converting the image data in such a way that a number of colors and a number of gradations in an image become predetermined numerical values. For example, the image acquisition unit 210 may convert image data representing a color image by a plurality of color components such as red (R), green (G), and blue (B) into image data representing a single-component grayscale image.

The condition acquisition unit 220 acquires camera information. Camera information is data including an imaging condition of an image acquired by the image acquisition unit 210. An imaging condition referred to herein is, for example, an installation angle of an imaging device. In addition, an imaging condition can include a parameter (a field angle or the like) of a lens of an imaging device, and an estimated range of a gaze at a time of capturing. Camera information is equivalent to one example of the first condition information according to the first example embodiment.

Camera information may be input together with image data. For example, camera information may be described as metadata included in image data. Alternatively, camera information may be input by an operation of a user. In this case, the condition acquisition unit 220 receives an operation of a user via a keyboard or a touch screen display.

The region extraction unit 230 extracts a particular region from image data. The region extraction unit 230 extracts a region necessary for gaze estimation by the gaze estimation unit 240. In the present example embodiment, the region extraction unit 230 particularly extracts a peripheral region of an eye out of a face image. Hereinafter, a region extracted by the region extraction unit 230 is referred to as an "eye region". An eye region is, for example, a rectangle of a predetermined size including both eyes of a human.

The region extraction unit 230 can extract an eye region, based on an image characteristic peculiar to a general face image. The region extraction unit 230 can extract an eye region by detecting, for example, an iris (a so-called pupil), a sclera (a so-called white of an eye), an inner canthus (a so-called inner corner of an eye), an outer canthus (a so-called outer corner of an eye), an eyebrow, or the like. For extraction of an eye region, it is possible to use a known feature detection technique such as a method described in PTL 3, for example.

The region extraction unit 230 may execute pre-processing dependent on a gaze estimation method. For example, when an extracted eye region is not horizontal, i.e., when height of a center of a right eye and height of a center of a left eye in an eye region do not coincide with each other, the region extraction unit 230 may rotate an image in such a way that the right eye and the left eye are horizontally located. The region extraction unit 230 may also magnify or reduce an image in such a way that a size of an eye region becomes a constant size. Known image processing is applicable to rotation processing, magnification processing (i.e., interpolation processing), and reduction processing (i.e., thinning processing) of an image. When such image processing is executed, scale and inclination of an eye region become stable, it thus becomes unnecessary to learn the scale and inclination, and therefore, it is possible to improve accuracy of gaze estimation.

The gaze estimation unit 240 estimates a gaze of a face included in a face image. More specifically, the gaze estimation unit 240 includes gaze estimators $241_1$, $241_2$, ..., and $241_n$. A value of n herein, i.e., a total number of gaze estimators is not limited to a particular numerical value when "2" or more. Hereinafter, the gaze estimators $241_1$, $241_2$, ..., and $241_n$ are generically called a "gaze estimator 241" when not needed to be differentiated from one another. The gaze estimation unit 240 is equivalent to one example of the estimation unit 110 according to the first example embodiment.

The gaze estimator 241 estimates a gaze by use of an eye region extracted by the region extraction unit 230. In the present example embodiment, the gaze estimator 241 is configured in such a way as to previously learn a gaze of an eye included in a face image by machine learning, and estimate a gaze by use of a result of the learning.

The gaze estimators $241_1$, $241_2$, ..., and $241_n$ each have different gaze estimation methods. For example, the gaze estimators $241_1$, $241_2$, ..., and $241_n$ each have different face images used as samples in machine learning. Alternatively, the gaze estimators $241_1$, $241_2$, ..., and $241_n$ may have different algorithms of machine learning.

The integration unit 250 integrates estimation results estimated by the gaze estimation unit 240, more specifically, the gaze estimators $241_1$, $241_2$, ..., and $241_n$. In other words, the integration unit 250 determines a gaze in a single direction, based on a plurality of gazes estimated by the gaze estimators $241_1$, $241_2$, ..., and $241_n$. The integration unit 250 is equivalent to one example of the determination unit 120 according to the first example embodiment.

The integration unit 250 integrates a plurality of gazes, based on camera information and learning information. Herein, learning information is data including a condition relating to learning of each of the gaze estimators $241_1$, $241_2$, ..., and $241_n$. Learning information represents, for example, an imaging condition of an imaging device used for learning of each of the gaze estimators $241_1$, $241_2$, ..., and $241_n$. It is assumed that learning information is stored in the data processing device 200. Learning information is equivalent to one example of the second condition information according to the first example embodiment.

The integration unit 250 integrates a plurality of gazes each estimated by each of the gaze estimators $241_1$, $241_2$, ..., and $241_n$, by weighted calculation using weights each determined for each of the gaze estimators $241_1$, $241_2$, ..., and $241_n$. In this instance, the integration unit 250 can determine a weight for each gaze by using camera information and learning information. Weighted calculation by the integration unit 250 is described in detail in a later-described operation example.

The output unit 260 outputs data (hereinafter also referred to as "gaze data".) indicating gazes integrated by the integration unit 250. Gaze data represents, for example, gazes integrated by the integration unit 250, i.e., directions determined by the integration unit 250, in accordance with a predetermined rule. Output by the output unit 260 may be supplying gaze data to another device such as a display device, or may be writing gaze data into a storage medium included in the data processing device 200.

A configuration of the data processing device 200 is as described above. Under this configuration, the data processing device 200 estimates a gaze, based on image data. The data processing device 200 operates, for example, as in the operation example below. However, a specific operation of the data processing device 200 is not limited to this operation example.

Figure 4:
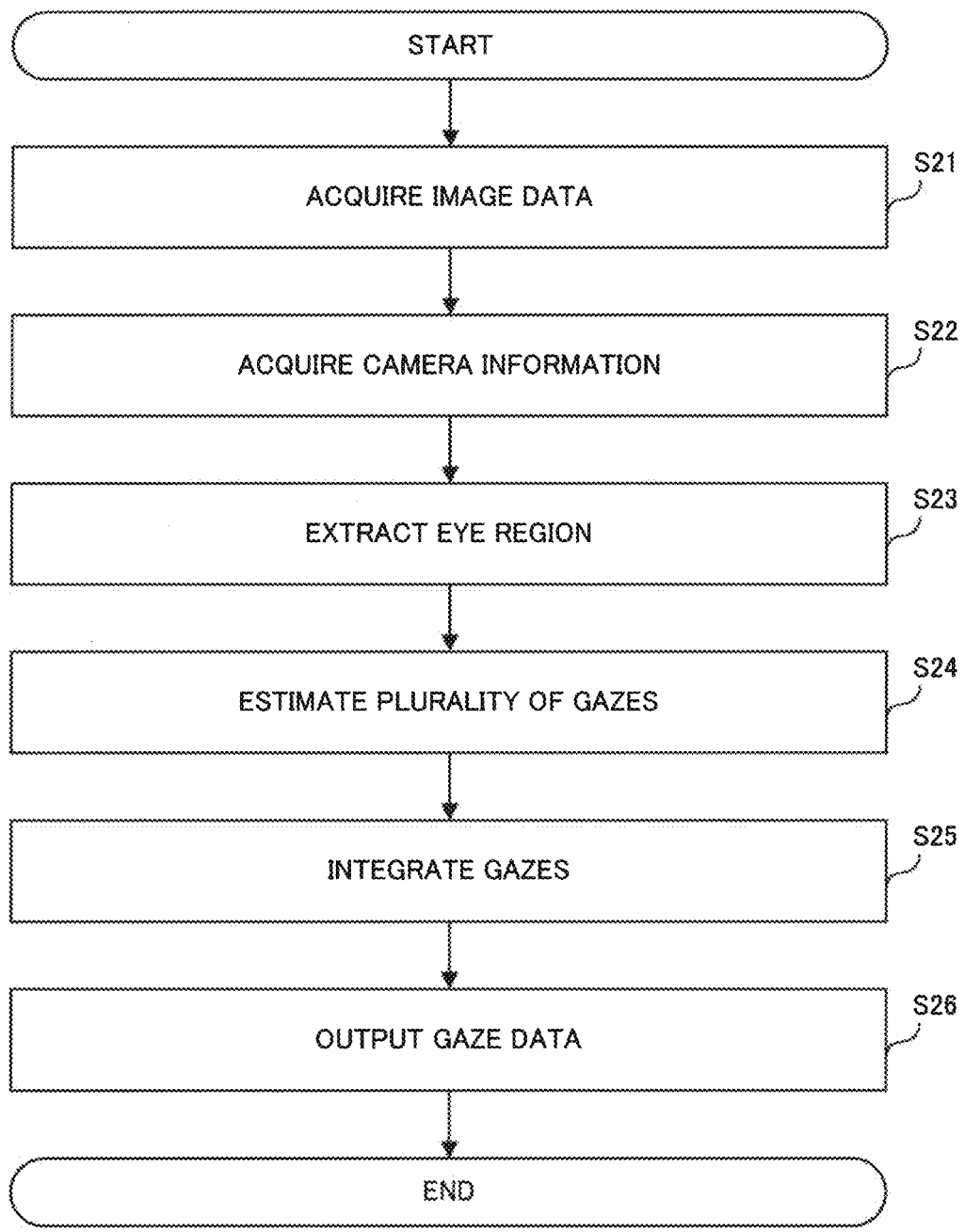
FIG. 4 is a flowchart illustrating an operation example of the data processing device.

FIG. 4 is a flowchart illustrating an operation example of the data processing device 200. The data processing device 200 can execute processing illustrated in FIG. 4 at appropriate timing such as timing specified by a user, or timing at which image data are transmitted from another device. In this example, it is assumed that an image represented by image data includes a face image. It is also assumed that camera information and learning information are installation angles of an imaging device. It is also assumed that a coordinate of an image referred to herein is represented by an orthogonal coordinate system in which a predetermined position is an origin.

In a step S21, the image acquisition unit 210 acquires image data. In a step S22, the condition acquisition unit 220 acquires camera information. Note that processing in the steps S21 and S22 may be executed in an order reverse to that in FIG. 4, or may be executed simultaneously (i.e., in parallel).

In a step S23, the region extraction unit 230 extracts an eye region by use of the image data acquired in the step S21. In this example, the region extraction unit 230 specifies a coordinate of a center of an iris of a right eye, and a coordinate of a center of an iris of a left eye. The region extraction unit 230 determines an eye region, based on these coordinates. For convenience of description, hereinafter, a coordinate of a center of an iris of a right eye is also referred to as a "central coordinate of a right eye", and a coordinate of a center of an iris of a left eye is also referred to as a "central coordinate of a left eye".

Specifically, the region extraction unit 230 designates, as a center of an eye region, a midpoint of a line segment connecting a central coordinate of a right eye and a central coordinate of a left eye. The region extraction unit 230 designates, as width of an eye region, length 2 times length (hereinafter also referred to as an "interpupillary distance".) of a line segment connecting a central coordinate of a right eye and a central coordinate of a left eye, and designates, as height of an eye region, length 0.75 times an interpupillary distance. The region extraction unit 230 cuts out, from an image, a rectangular region defined by the center, width, and height determined in this way, as an eye region.

Furthermore, the region extraction unit 230 may execute pre-processing of correcting inclination, width, and height of an eye region, in such a way that subsequent processing becomes easier. More specifically, when a central coordinate of a right eye and a central coordinate of a left eye are not horizontal, the region extraction unit 230 makes these coordinates horizontal, and when a number of pixels in a width direction and a height direction of an eye region is not a predetermined number of pixels, the region extraction unit 230 magnifies or reduces the eye region.

Figure 5:
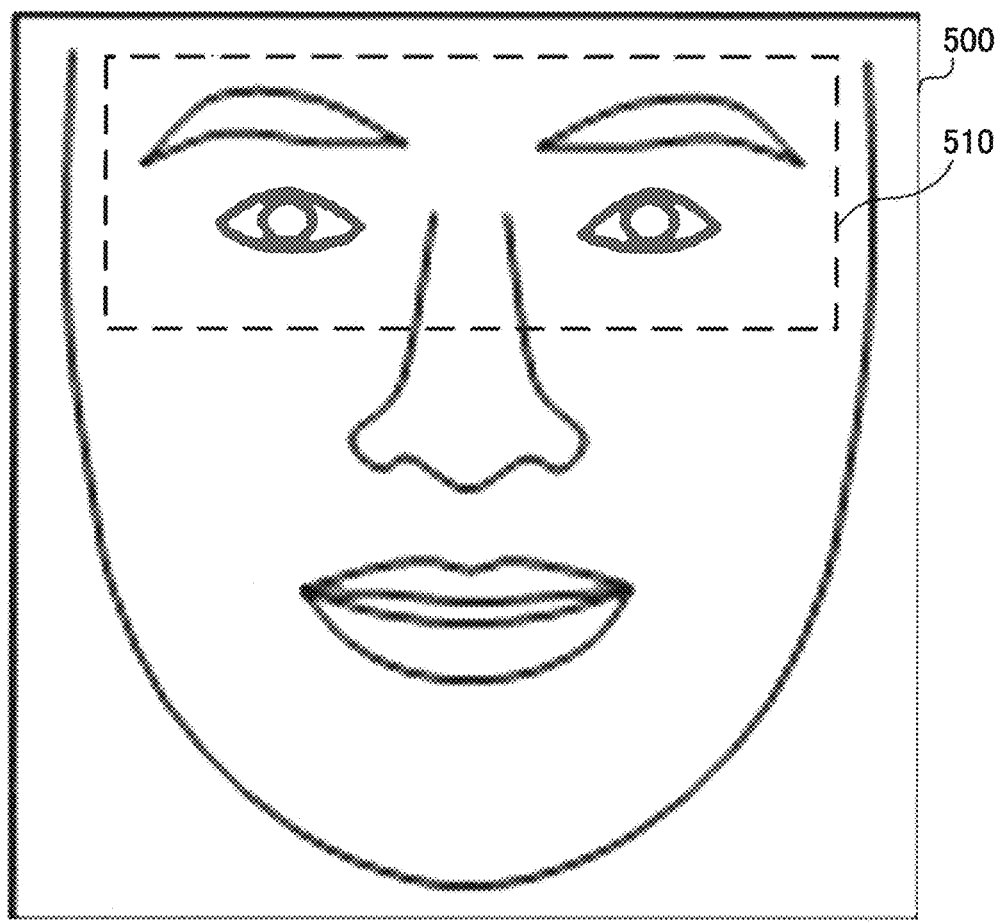
FIG. 5 is a diagram illustrating one example of a face image.
Figure 6:
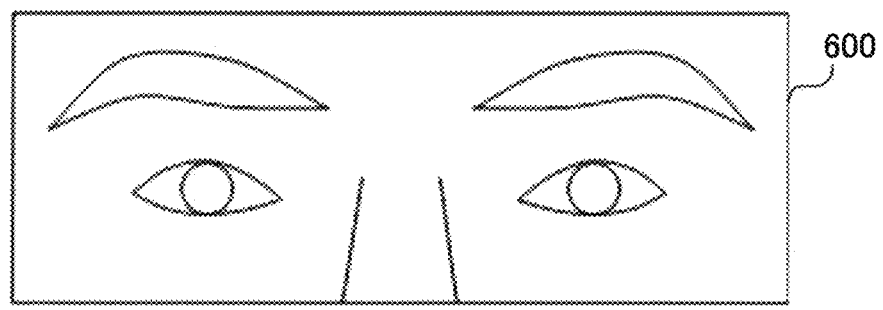
FIG. 6 is a diagram illustrating one example of an eye region.

FIG. 5 is a diagram illustrating one example of a face image. FIG. 6 is a diagram illustrating one example of an eye region extracted from this face image. An eye region 600 illustrated in FIG. 6 is equivalent to a part of a face image 500 illustrated in FIG. 5. Specifically, the eye region 600 is equivalent to a region 510 surrounded by a broken line in the face image 500. However, when the above-described preprocessing is performed, a number of pixels and inclination of the eye region 600 do not necessarily coincide with those of the region 510.

In a step S24, the gaze estimation unit 240 estimates a gaze, based on the eye region extracted in the step S23. The gaze estimation unit 240 estimates a gaze by use of the gaze estimators $241_1$ to $241_n$ learned in advance. In this example, the gaze estimators $241_1$ to $241_n$ estimate a gaze, based on an image characteristic amount detected from an eye region.

An image characteristic amount in this example is a characteristic amount relating to gradient of luminance of an image. As a characteristic amount relating to gradient of luminance, for example, a histograms of oriented gradients (HOG) characteristic amount is known. An image characteristic amount in this example indicates a direction and a magnitude of a change of luminance in an eye region by a predetermined number of dimensions (e.g., several hundred to several thousand). Hereinafter, this image characteristic amount is also represented by a column vector f having a predetermined number of elements.

The gaze estimators $241_1$ to $241_n$ calculate a gaze $(g_x, g_y)$ by use of Equation (1) below. Herein, the gaze $(g_x, g_y)$ indicates an orientation of a gaze referenced to an orientation of a face, by a horizontal angle and an elevation/depression angle. Of the gaze, $g_x$ represents a horizontal angle, and satisfies $-90 \leq g_x \leq 90$ (a unit is [deg]). Moreover, $g_y$ represents an elevation/depression angle, and satisfies $-90 \leq g_y \leq 90$ (a unit is [deg]).

[Equation 1]

$$\begin{pmatrix} g_x \\ g_y \end{pmatrix} = \begin{pmatrix} u_x \\ u_y \end{pmatrix} f \quad (1)$$

The gaze $(g_x, g_y)$ is a gaze which is referenced to a case where $(g_x, g_y) = (0, 0)$, i.e., which is directed immediately forward with respect to a face, and represents a deviation from an immediately forward direction by a horizontal angle and an elevation/depression angle. For example, $(g_x, g_y) = (0, +90)$ when a gaze is directed immediately upward, and $(g_x, g_y) = (0, -90)$ when a gaze is directed immediately downward. Moreover, $(g_x, g_y) = (+90, 0)$ when a gaze is directed immediately sideward (rightward), and $(g_x, g_y) = (-90, 0)$ when a gaze is directed immediately sideward (leftward).

Note that a forward orientation referred to herein depends on an orientation of a face represented by a face image. In other words, forward referred to herein changes depending on an orientation of a face. Therefore, a direction in which a captured person is actually seeing with an eye is not specified only by the gaze $(g_x, g_y)$, but is specified by the gaze $(g_x, g_y)$ and an orientation of a face of the person.

In Equation (1), $u_x$ and $u_y$ are weight vectors. Each of the weight vectors $u_x$ and $u_y$ is a row vector having a same number of elements as the image characteristic amount f, and an inner product of each of the weight vectors $u_x$ and $u_y$ and the image characteristic amount f can be calculated. The weight vectors $u_x$ and $u_y$ can differ depending on each of the gaze estimators $241_1$ to $241_n$. The weight vectors $u_x$ and $u_y$ can be learned in advance by a known technique such as support vector regression or linear regression by a least squares method. Learning in the gaze estimators $241_1$ to $241_n$ is generally executed by preparing a large number of combinations of an image of an eye region extracted as in the step S23 and information (i.e., correct-answer information) indicating an actual gaze of the image.

In this example, the gaze estimators $241_1$ to $241_n$ each execute learning by use of an image of an eye region having a different imaging condition. Specifically, for learning of the gaze estimators $241_1$ to $241_n$, images of an eye region each captured by an imaging device at a different installation angle are used.

Figure 7:
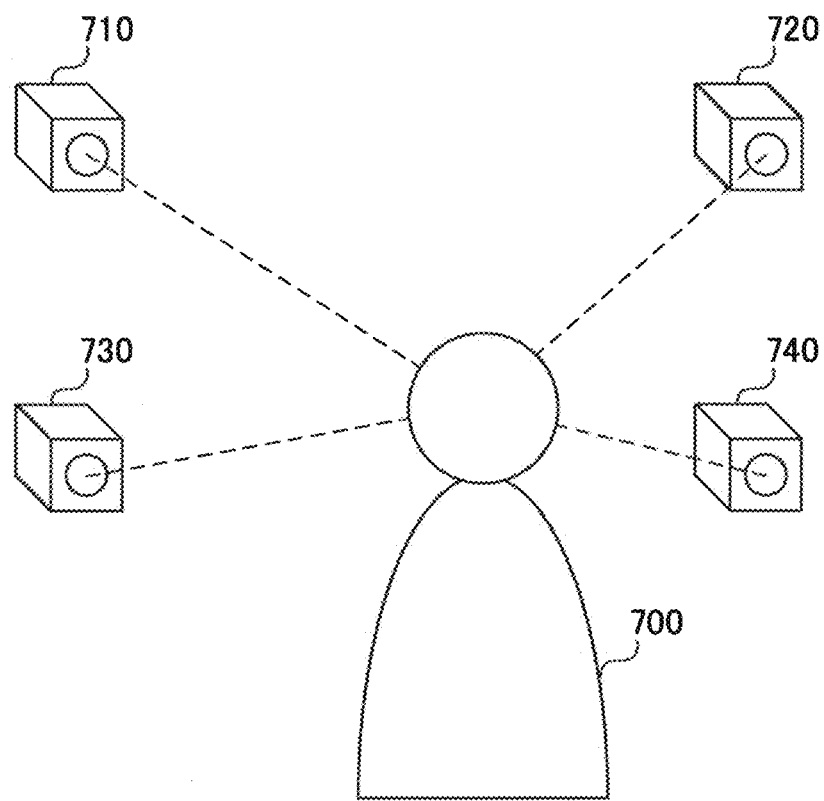
FIG. 7 is a conceptual diagram for describing an imaging condition of an image of an eye region.

FIG. 7 is a conceptual diagram for describing an imaging condition of an image of an eye region. Herein, it is assumed that a number of gaze estimators 241 (i.e., a value of n) is "4". In the example of FIG. 7, cameras 710, 720, 730, and 740 are imaging devices which each capture a face image of a person 700. The camera 710 captures a face image from an upper right side. The camera 720 captures a face image from an upper left side. The camera 730 captures a face image from a lower right side. The camera 740 captures a face image from a lower left side. Note that the person 700 may be a person differing from image to image, or may be a same person in all images. Moreover, it is assumed that the person 700 faces in a same direction (forward) during capturing.

The gaze estimator $241_1$ uses, for learning, a face image captured by the camera 710. The gaze estimator $241_2$ uses, for learning, a face image captured by the camera 720. The gaze estimator $241_3$ uses, for learning, a face image captured by the camera 730. The gaze estimator $241_4$ uses, for learning, a face image captured by the camera 740. Accordingly, the gaze estimators $241_1$ to $241_4$ are different from one another in installation angles of the imaging devices associated with the face images used for learning.

The gaze estimators $241_1$ to $241_n$ are different in conditions of machine learning (herein, imaging conditions of face images used for learning), and therefore, estimation results can differ even when estimating gazes by use of an image of a same eye region. In other words, since the gaze estimators $241_1$ to $241_n$ can differ from one another in the weight vectors $u_x$ and $u_y$ in Equation (1), there is a possibility that the gaze $(g_x, g_y)$ can differ even when the image characteristic amount f has a same value. Hereinafter, a gaze estimated by the gaze estimator $241_1$ is also referred to as $(g^{(1)}_x, g^{(1)}_y)$, a gaze estimated by the gaze estimator $241_2$ is also referred to as $(g^{(2)}_x, g^{(2)}_y)$, ..., and a gaze estimated by the gaze estimator $241_n$ is also referred to as $(g^{(n)}_x, g^{(n)}_y)$.

In a step S25, the integration unit 250 integrates the gazes $(g^{(1)}_x, g^{(1)}_y))$ to $(g^{(n)}_x, g^{(n)}_y)$ estimated in the step S24. In other words, the integration unit 250 calculates a single gaze, based on the gazes $(g^{(1)}_x, g^{(1)}_y)$ to $(g^{(n)}_x, g^{(n)}_y)$ estimated in the step S24. Herein, the integration unit 250 calculates a weight, based on camera information and learning information. Herein, camera information and learning information are installation angles of an imaging device.

The integration unit 250 calculates a weight $w_i$ corresponding to the gaze estimator $241_i$ by use of Equation 2 below. Herein, each of $c_i$, $c_j$, and $c_t$ is a vector representing an installation angle of an imaging device. $c_i$ (or $c_j$) indicates an average value of angles each formed by each of directions of a face represented by a plurality of face images used for learning of the gaze estimator $241_i$ (or $241_j$), and an optical axis direction of an imaging device capturing each the face images. On the other hand, $c_i$ indicates an angle formed by a direction of a face represented by a face image included in input image data, and an optical axis direction of an imaging device capturing the face image. $c_i$ and $c_j$ are one example of learning information. On the other hand, $c_t$ is one example of camera information. Moreover, α is an appropriate coefficient more than 0.

[Equation 2]

$$w_i = \frac{1}{\sum_{j=1}^{n} \exp(-\alpha\|c_j - c_t\|)} \exp(-\alpha\|c_i - c_t\|) \quad (2)$$

For example, when it is assumed that n=2, i.e., a number of gaze estimators 241 is 2, weights $w_1$ and $w_2$ can be represented by Equations (3) and (4) below. Note that the smaller a difference between the learning information $c_i$ and the camera information $c_t$ is, the greater the weight $w_i$ becomes.

[Equation 3]

$$w_1 = \frac{\exp(-\alpha\|c_1 - c_t\|)}{\exp(-\alpha\|c_1 - c_t\|) + \exp(-\alpha\|c_2 - c_t\|)} \quad (3)$$

[Equation 4]

$$w_2 = \frac{\exp(-\alpha\|c_2 - c_t\|)}{\exp(-\alpha\|c_1 - c_t\|) + \exp(-\alpha\|c_2 - c_t\|)} \quad (4)$$

After calculating the weight $w_i$ in this way, the integration unit 250 calculates a gaze $(G_x, G_y)$ in accordance with Equation (5) below. As presented by Equation (5), the gaze $(G_x, G_y)$ is a weighted average of the gazes $(g^{(1)}_x, g^{(1)}_y)$ to $(g^{(n)}_x, g^{(n)}_y)$. Note that a denominator on a right side of Equation (5) is "1" herein (refer to Equation (2)).

[Equation 5]

$$\begin{pmatrix} G_x \\ G_y \end{pmatrix} = \frac{\sum_{j=1}^{n} w_j \begin{pmatrix} g^{(j)}_x \\ g^{(j)}_y \end{pmatrix}}{\sum_{j=1}^{n} w_j} \quad (5)$$

In a step S26, the output unit 260 outputs gaze data indicating the gaze $(G_x, G_y)$ calculated by the integration unit 250. The gaze data are visualized by, for example, a display device. A gaze indicated by gaze data may be displayed by a numerical value, or may be displayed in such a way that an arrow indicating the gaze is superimposed on a face image.

Figure 8:
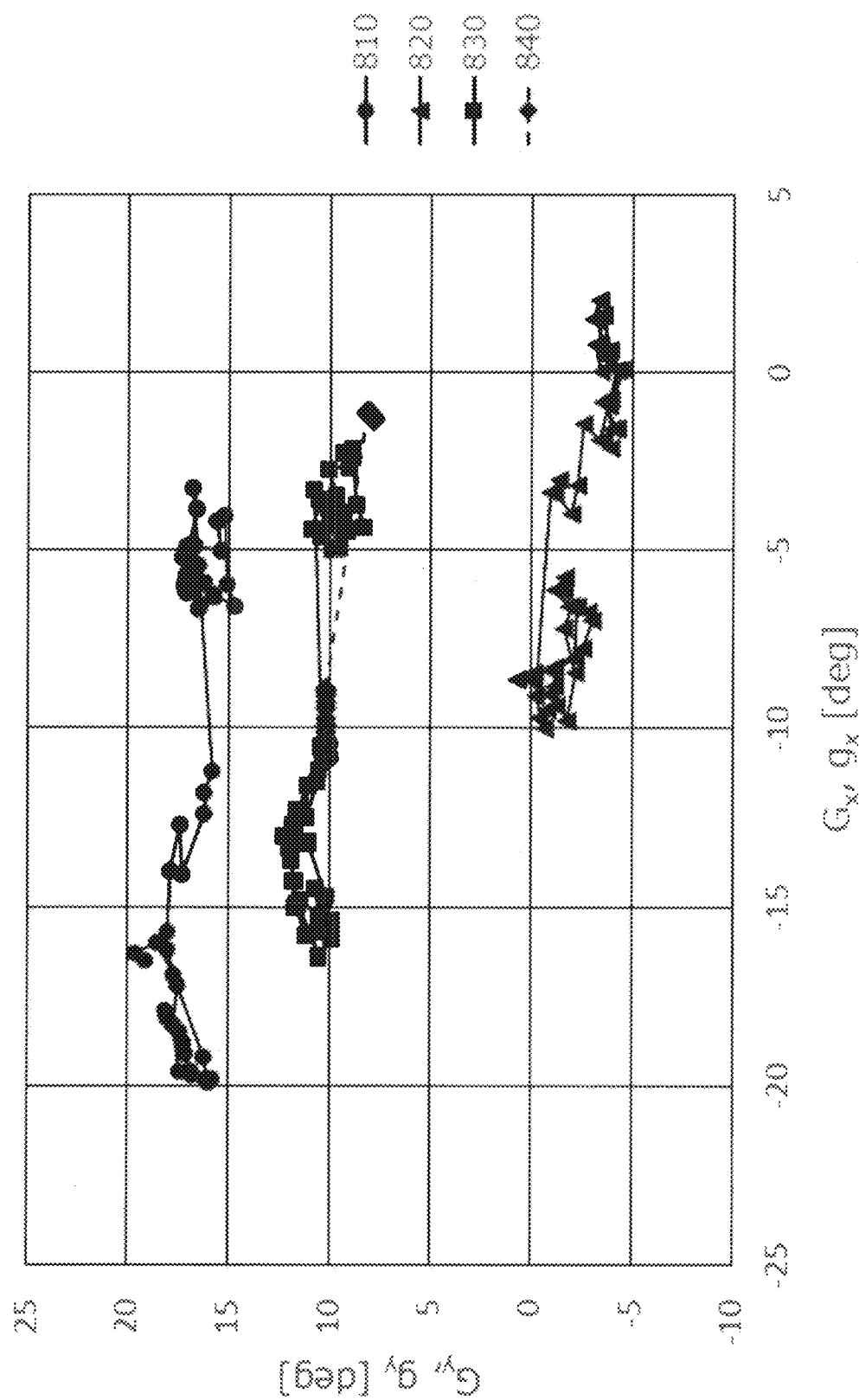
FIG. 8 is a diagram illustrating one example of an advantageous effect of an example embodiment.

FIG. 8 is a diagram illustrating one example of an advantageous effect of the present example embodiment. In this example, a number of gaze estimators 241 is 2. This example is an example in which a gaze is estimated by use of a moving image that captures one subject watching two watching points in order. Note that learning information (installation angle) associated with the gaze estimator $241_1$ is (+2.3[deg],+5.5[deg]). Moreover, learning information (installation angle) associated with the gaze estimator $241_2$ is (+1.2[deg],−22.7[deg]). In addition, camera information (installation angle) is (0[deg],0[deg]). The coefficient α is "0.04" herein.

In FIG. 8, a graph 810 represents a gaze $(g^{(1)}_x, g^{(1)}_y)$ estimated by the gaze estimator $241_1$. A graph 820 represents a gaze $(g^{(2)}_x, g^{(2)}_y)$ estimated by the gaze estimator $241_2$. A graph 830 represents the gaze $(G_x, G_y)$ integrated by the integration unit 250. A graph 840 represents an actual gaze of a subject.

As illustrated in FIG. 8, the gaze $(G_x, G_y)$ integrated by the integration unit 250 has a smaller margin of error with regard to the actual gaze, than the gaze $(g^{(1)}_x, g^{(1)}_y)$ estimated by the gaze estimator $241_1$ and the gaze $(g^{(2)}_x, g^{(2)}_y)$ estimated by the gaze estimator $241_2$. Therefore, it can be said that the data processing device 200 is improved in accuracy of gaze estimation, as compared with a case of using a single gaze estimator 241.

In this example, when the graph 810, i.e., the gaze $(g^{(1)}_x, g^{(1)}_y)$ is compared with the graph 820, i.e., the gaze $(g^{(2)}_x, g^{(2)}_y)$, it can be said that the gaze $(g^{(1)}_x, g^{(1)}_y)$ is an estimation result closer to the actual gaze (graph 840). Herein, when camera information is compared with learning information associated with the gaze estimators $241_1$ and $241_2$, it can be said that the learning information associated with the gaze estimator $241_1$ has a smaller difference from the camera information. According to the weighted additions (refer to Equations (2) to (5)) in the present example embodiment, a gaze estimator 241 having a smaller difference between learning information and camera information has a greater weight w Therefore, a gaze represented by gaze data, i.e., a final estimation result, becomes closer to a gaze estimated by a gaze estimator 241 an installation angle of which included in an imaging condition is closer.

In this example, it can be said that estimation accuracy of a gaze estimator 241 depends on an imaging condition in advance learning, and a face image being an estimation target by the data processing device 200, in other words, an imaging condition of a face image represented by input image data. More specifically, it can be said that estimation accuracy of a gaze estimator 241 depends on an approximation degree of a relative position relation (installation angle) between a face image in advance learning and an imaging device, and a relative position relation (installation angle) between a face image being an estimation target and an imaging device that captures the face image. However, a relative position relation between a face image being an estimation target and an imaging device is not necessarily always constant, and varies depending on an imaging method in some cases.

According to the gaze estimation method in the present example embodiment, by executing the weighted additions as in Equations (2) to (5), it is possible to integrate estimation results by a plurality of gaze estimators 241 learned by use of different imaging conditions. Therefore, according to the gaze estimation method in the present example embodiment, gaze estimation with satisfactory accuracy is possible even when an imaging condition of a face image represented by input image data is not coincident with imaging conditions in advance learning of a plurality of gaze estimators 241. In addition, according to the gaze estimation method in the present example embodiment, gaze estimation with satisfactory accuracy is possible even when a relative position relation between a face image represented by input image data and an imaging device is not constant.

As described above, the data processing device 200 according to the present example embodiment has a configuration which estimates a gaze of a face included in a face image by a plurality of gaze estimators 241, and integrates an estimated plurality of gazes. With this configuration, the data processing device 200 can exert an action and an advantageous effect similar to those of the gaze estimation device 100 according to the first example embodiment.

Moreover, the data processing device 200 has a configuration which integrates gazes by executing weighted calculation conforming to a weight determined depending on learning information and camera information representing imaging conditions. This configuration enables a weight dependent on an imaging condition to be given to a plurality of gazes estimated by a plurality of gaze estimators 241. Therefore, as compared with a case where such a weight is not given, the data processing device 200 can improve accuracy of gaze estimation.

Furthermore, the data processing device 200 has a configuration which determines a weight dependent on a result of comparison between learning information and camera information representing imaging conditions. More specifically, the data processing device 200 makes a weight greater for a gaze in which an installation angle of an imaging device during learning of a gaze estimator 241 is closer to an installation angle of an imaging device capturing a face image represented by input image data, among a plurality of gazes estimated by a plurality of gaze estimators 241. With such a configuration, the data processing device 200 can bring a gaze represented by output gaze data closer to a gaze estimated by a gaze estimator 241 an installation angle of which is closer.

Modification Examples

For example, it is possible to apply the following modifications to the example embodiments described above. It is also possible to suitably combine these modification examples as needed.

Modification Example 1

The determination unit 120 can estimate a direction of a face by using a known face orientation estimation technique. The determination unit 120 may calculate an installation angle of an imaging device, based on an angle formed by a direction of a face estimated in this way and an optical axis direction of an imaging device.

Modification Example 2

Camera information and learning information may include information indicating a kind of imaging device used for capturing of a face image. A kind of imaging device referred to herein represents, for example, a model of an imaging device, or a wavelength range of light to which an imaging device is sensitive.

For example, there is a case where a visible light camera which captures by visible light and a near-infrared light camera which captures by near-infrared light are included in an imaging device. In such a case, when a visible light camera and a near-infrared light camera are also included in an imaging device used for learning of a gaze estimator 241, there is a possibility that an imaging device used for capture of an input face image differs from an imaging device used for learning. For example, when an imaging device used for capture of an input face image is a near-infrared light camera, it can be said that an estimation result by a gaze estimator 241 in which an imaging device used for learning is a near-infrared light camera has a high possibility of being reliable (i.e., accuracy is guaranteed).

In such a case, the integration unit 250 makes greater a weight $w_i$ corresponding to a gaze estimator 241, in which a kind of imaging device used for capture of an input face image coincides with a kind of imaging device used for learning, and the integration unit 250 makes smaller a weight $w_i$ corresponding to a gaze estimator 241, in which a kind of imaging device used for capture of an input face image does not coincide with a kind of imaging device used for learning. In this way, it is possible to more strongly reflect, in gaze data, an estimation result of a gaze estimator 241, in which an imaging device similar to an imaging device used for capture of an input face image is used for learning.

Moreover, camera information and learning information may be parameters of an optical system of an imaging device. For example, camera information and learning information may include, as parameters, field angles in a horizontal direction and a vertical direction of a lens. In this case, by use of, as camera information and learning information, a vector in which such parameters are elements, the integration unit 250 can calculate a weight by calculation similar to Equation (2).

Modification Example 3

A method of weighted calculation in the second example embodiment is not limited to the above-described operation example. For example, the integration unit 250 may integrate the gazes $(g^{(1)}_x, g^{(1)}_y)$ to $(g^{(n)}_x, g^{(n)}_y)$ without using a part of the weight $w_i$ calculated by Equation (2). Specifically, the integration unit 250 may replace, with "0", one other than those that are equal to or more than a predetermined threshold value (or a predetermined number of weights $w_i$ in descending order of value) among the weights $w_i$. This replacement is equivalent to discarding those that less affect a final estimation result among the weights $w_i$. Moreover, in this case, the integration unit 250 may recalculate a ratio (a denominator of Equation (2)) of each weight in such a way that a total of weights $w_i$ after discard becomes "1".

Moreover, in Equation (2), the integration unit 250 may use another function which monotonically decreases with regard to an increase of $\|c_i - c_t\|$, instead of $\exp(-\alpha\|c_i - c_t\|)$. For example, the integration unit 250 may calculate a weight $w_i$ by use of Equation (6) below. Herein, max(a,b) represents a function which returns a greater value of either a or b. Moreover, β is a constant of 0 or more.

[Equation 6]

$$w_i = \frac{1}{\sum_{j=1}^{n} \max(0, -\alpha\|c_j - c_t\| + \beta)} \max(0, -\alpha\|c_i - c_t\| + \beta) \quad (6)$$

Alternatively, the integration unit 250 may calculate the gaze $(G_x, G_y)$ in Equation (5) after discarding parts of the gazes $(g^{(1)}_x, g^{(1)}_y)$ to $(g^{(n)}_x, g^{(n)}_y)$. For example, when an outlier is included in the gazes $(g^{(1)}_x, g^{(1)}_y)$ to $(g^{(n)}_x, g^{(n)}_y)$, the integration unit 250 may execute the calculation in Equation (5), excluding the outlier. This is because a gaze equivalent to an outlier is considered to be an unsuccessfully estimated gaze. An outlier referred to herein is a value greatly departing from other values among the gazes $(g^{(1)}_x, g^{(1)}_y)$ to $(g^{(n)}_x, g^{(n)}_y)$. For example, an outlier is specified based on a Euclidean distance between gazes when the gazes ($g^{(1)}_x$, $g^{(1)}_y$) to ($g^{(n)}_x, g^{(n)}_y$) are regarded as vectors.

Modification Example 4

As described above, learning information and camera information can include a range of an estimated gaze. A range of a gaze referred to herein indicates a range of a gaze to be estimated in camera information, and indicates a range of a gaze used for learning in a gaze estimator 241 in learning information. A range of a gaze represents, for example, a deviation from an immediately forward direction by a numerical value ranging from −90 to +90 [deg], in a way similar to the gaze ($g_x, g_y$). Learning information and camera information may represent a range of a gaze by both a horizontal angle and an elevation/depression angle, or by one of these angles.

When such learning information and camera information are used, the integration unit 250 can calculate a weight, based on a ratio (hereinafter also referred to as an "overlap ratio".) at which ranges of gazes overlap. Herein, an overlap ratio represents a ratio of a range of a gaze included in at least either learning information or camera information, and a range of a gaze included in both learning information and camera information.

For example, when a range of a gaze represented by learning information completely coincides with a range of a gaze represented by camera information, an overlap ratio is "1.0". On the other hand, when a range of a gaze represented by learning information does not at all coincide with a range of a gaze represented by camera information, an overlap ratio is "0". More specifically, when a range of a gaze in a horizontal direction represented by learning information of the gaze estimator $241_1$ is −10 to +5 [deg], and a range of a gaze in a horizontal direction represented by camera information is −10 to +10 [deg], an overlap ratio in a horizontal direction is "0.75 (=15/20)".

When such learning information and camera information are used, the integration unit 250 can use overlap ratios in a horizontal direction and a vertical direction as the learning information $c_i$ and $c_j$ and the camera information $c_t$ in Equation (2). The integration unit 250 may use an overlap ratio instead of an installation angle of an imaging angle, or may use an overlap ratio in addition to an installation angle of an imaging angle. For example, when both an installation angle of an imaging angle and an overlap ratio are used, the learning information $c_i$ and $c_j$ and the camera information $c_t$ become a vector having four components (horizontal and vertical components of an installation angle, and horizontal and vertical components of an overlap ratio).

Modification Example 5

The region extraction unit 230 does not have to specify central coordinates of right and left eyes and an eye region, by calculation. For example, central coordinates of right and left eyes and an eye region may be input by a user. In this case, the data processing device 200 can specify central coordinates of right and left eyes and an eye region, based on an input of a user.

Modification Example 6

A shape of an eye region is not necessarily limited to a rectangular shape. For example, the region extraction unit 230 may exclude a region (e.g., a region of a nose) which does not directly affect estimation of a gaze, from the above-described eye region (refer to FIG. 6). Moreover, an eye region does not necessarily have to include both eyes. For example, the region extraction unit 230 may extract, as an eye region, a region which includes either one of right or left eye, and does not include the other.

Modification Example 7

Learning by the gaze estimation unit 240 is not limited to the above-described example. For example, the gaze estimation unit 240 may learn a non-linear function serving to estimate a gaze by a group learning algorithm such as a random forest.

Modification Example 8

A purpose of a gaze estimated by the gaze estimation device 100 (or the data processing device 200) is not particularly limited. For example, the gaze estimation device 100 may be applied to a system which estimates a gaze of a person captured by a surveillance camera disposed in a retail store such as a convenience store, and detects a suspicious person. Moreover, the gaze estimation device 100 may also be applied to a system which speculates, based on a gaze of a user at a screen displaying information, interest and concern of the user. Alternatively, the gaze estimation device 100 may be applied to an electronic device being operable by movement of a gaze, or drive support of an automobile or the like.

Modification Example 9

A specific hardware configuration of a device (the gaze estimation device 100 or the data processing device 200) according to the present disclosure includes various variations, and is not limited to a particular configuration. For example, the device according to the present disclosure may be achieved by use of software, or may be configured to share various kinds of processing by use of a plurality of pieces of hardware.

Figure 9:
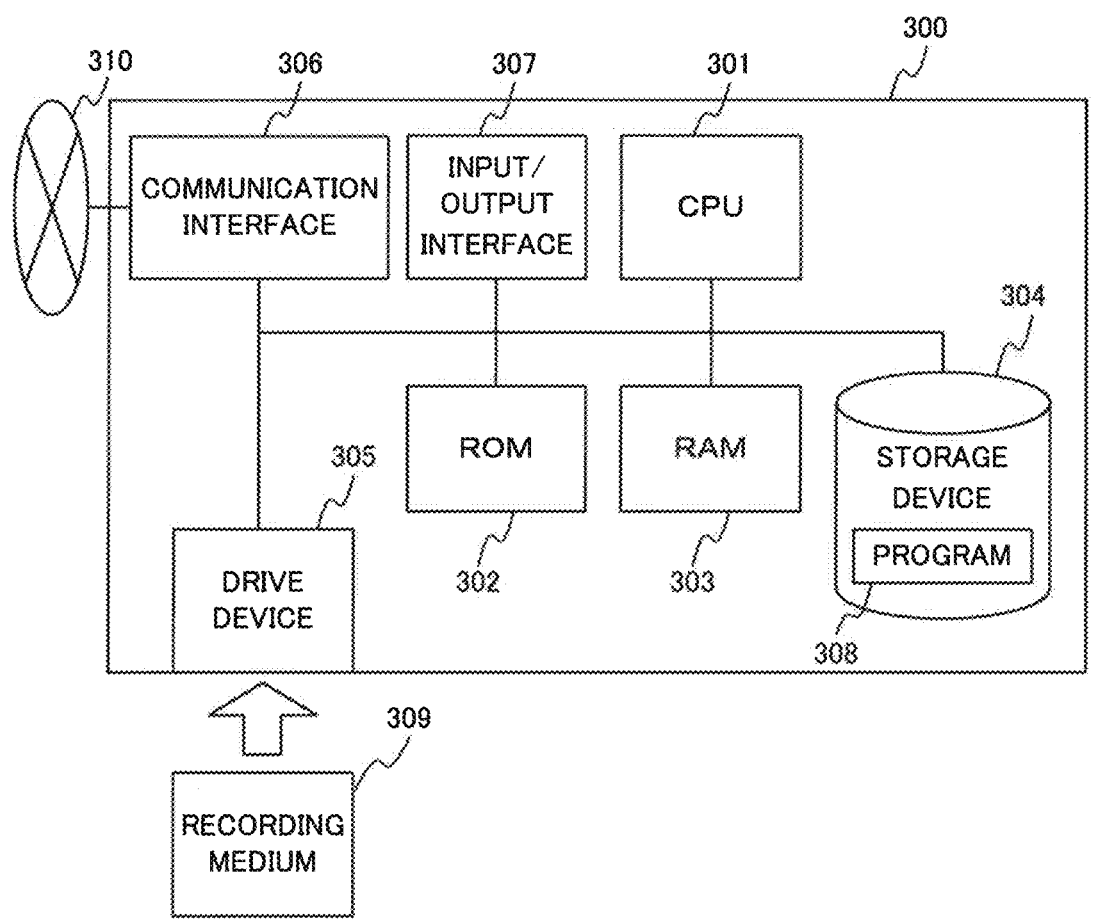
FIG. 9 is a block diagram illustrating one example of a hardware configuration of a computer device.

FIG. 9 is a block diagram illustrating one example of a hardware configuration of a computer device 300 which achieves the device according to the present disclosure. The computer device 300 is configured to include a central processing unit (CPU) 301, a read only memory (ROM) 302, a random access memory (RAM) 303, a storage device 304, a drive device 305, a communication interface 306, and an input/output interface 307. The device according to the present disclosure can be achieved by a configuration (or a part thereof) illustrated in FIG. 9.

The CPU 301 executes a program 308 by use of the RAM 303. The program 308 may be stored in the ROM 302. Moreover, the program 308 may be recorded in a recording medium 309 such as a memory card, and read by the drive device 305, or may be transmitted from an external device via a network 310. The communication interface 306 exchanges data with an external device via the network 310. The input/output interface 307 exchanges data with peripheral equipment (an input device, a display device, or the like). The communication interface 306 and the input/output interface 307 can function as components serving to acquire and output data.

Note that a component of a device according to the present disclosure may be configured by a single circuitry (a processor or the like), or may be configured by a combination of a plurality of circuitries. A circuitry referred to herein may be either dedicated or general-purpose. For example, a part of a device according to the present disclosure may be achieved by a dedicated processor, and another part may be achieved by a general-purpose processor The configuration described as a single device in the above-described example embodiments may be distributedly provided in a plurality of devices. For example, the gaze estimation device 100 may be achieved by cooperation of a plurality of computer devices by use of a cloud computing technique or the like. Moreover, the gaze estimators $241_1$ to $241_n$ may be achieved by computer devices different from one another.

The present invention has been described above with the above-described example embodiments and modification examples as exemplary examples. However, the present invention is not limited to these example embodiments and modification examples. The present invention can include an example embodiment to which various modifications and applications that can be known to a so-called person skilled in the art are applied within the scope of the present invention. Moreover, the present invention can include an example embodiment in which matters described in the present description are suitably combined or replaced as needed. For example, a matter described by use of a particular example embodiment is also applicable to another example embodiment as far as no inconsistency arises.

[Supplementary Notes]

A part or all of the present disclosure may also be described as in the following supplementary notes. However, the present disclosure is not necessarily limited to aspects of the supplementary notes.

[Supplementary Note 1]

A gaze estimation device, including:

an estimation means for estimating a gaze of a face included in a face image with a plurality of estimators; and a determination means for determining a gaze of the face, based on first condition information including a condition relating to capture of the face image, a plurality of pieces of second condition information each including the condition associated with one of the plurality of estimators, and the estimated plurality of gazes.

[Supplementary Note 2]

The gaze estimation device according to supplementary note 1, wherein the condition includes an imaging condition by imaging means.

[Supplementary Note 3]

The gaze estimation device according to supplementary note 1 or 2, wherein the condition includes a range of a gaze to be estimated.

[Supplementary Note 4]

The gaze estimation device according to any one of supplementary notes 1 to 3, wherein the determination means executes weighted calculation conforming to a weight determined for each of a plurality of gazes estimated by the plurality of estimators, and determined depending on the second condition information associated with the estimator and the first condition information.

[Supplementary Note 5]

The gaze estimation device according to supplementary note 4, wherein the determination means determines the weight, based on a result of comparison between the second condition information and the first condition information.

[Supplementary Note 6]

The gaze estimation device according to supplementary note 5, wherein the determination means makes the weight greater as the second condition information is closer to the first condition information.

[Supplementary Note 7]

The gaze estimation device according to any one of supplementary notes 1 to 6, wherein the plurality of estimators are learned based on face images different in the condition from one another.

[Supplementary Note 8]

The gaze estimation device according to any one of supplementary notes 1 to 7, further including:

a first acquisition means for acquiring the face image;

a second acquisition means for acquiring the first condition information;

an extraction means for extracting a peripheral region of an eye from the acquired face image; and an output means for outputting gaze information indicating a gaze determined by the determination means, wherein the estimation means estimates a gaze of the face by use of the region in the face image.

[Supplementary Note 9]

A gaze estimation method, including:

estimating a gaze of a face included in a face image with a plurality of estimators; and determining a gaze of the face, based on first condition information including a condition relating to capture of the face image, a plurality of pieces of second condition information each including the condition associated with one of the plurality of estimators, and the estimated plurality of gazes.

[Supplementary Note 10]

The gaze estimation method according to supplementary note 9, wherein the first condition information and the second condition information each include information indicating an imaging condition by imaging means.

[Supplementary Note 11]

A computer-readable program recording medium recording a program which causes a computer to execute:

processing of estimating a gaze of a face included in a face image with a plurality of estimators; and processing of determining a gaze of the face, based on first condition information including a condition relating to capture of the face image, a plurality of pieces of second condition information each including the condition associated with one of the plurality of estimators, and the estimated plurality of gazes.

[Supplementary Note 12]

The program recording medium according to supplementary note 11, wherein the first condition information and the second condition information each include information indicating an imaging condition by imaging means.

REFERENCE SIGNS LIST

100 Gaze estimation device
110 Estimation unit
120 Determination unit
200 Data processing device
210 Image acquisition unit
220 Condition acquisition unit
230 Region extraction unit
240 Gaze estimation unit
241 Gaze estimator 250 Integration unit
260 Output unit
300 Computer device

The invention claimed is:

1. A gaze estimation device, comprising:
at least one memory storing instructions; and
at least one processor configured to execute the instructions to perform:
   estimating a gaze of a face included in a face image with a plurality of estimators; and
   determining a gaze of the face, based on first condition information including a condition relating to capture of the face image, a plurality of pieces of second condition information each including the condition associated with one estimator the plurality of estimators, and the estimated plurality of gazes, wherein the condition includes a range of the gaze to be estimated; and
   executing weighted calculation conforming to a weight determined for each of a plurality of gazes estimated by the plurality of estimators, and determined depending on the second condition information associated with the one estimator and the first condition information; wherein the weight is determined based on an overlap ratio at which ranges of gazes overlap.

2. The gaze estimation device according to claim 1, wherein
the condition includes an imaging condition by an imaging device.

3. The gaze estimation device according to claim 1, wherein
the at least one processor is configured to execute the instructions to perform:
   determining the weight, based on a result of comparison between the second condition information and the first condition information.

4. The gaze estimation device according to claim 3, wherein
the at least one processor is configured to execute the instructions to perform:
   making the weight greater as the second condition information is closer to the first condition information.

5. The gaze estimation device according to claim 1, wherein:
the at least one processor is further configured to execute the instructions to perform:
   acquiring the face image;
   acquiring the first condition information;
   extracting a peripheral region of an eye from the acquired face image; and
   outputting gaze information indicating a gaze, and estimating the gaze of the face by use of the peripheral region in the face image.

6. A gaze estimation method, comprising:
estimating a gaze of a face included in a face image with a plurality of estimators; and
determining a gaze of the face, based on first condition information including a condition relating to capture of the face image, a plurality of pieces of second condition information each including the condition associated with one estimator the plurality of estimators, and the estimated plurality of gazes, wherein the condition includes a range of the gaze to be estimated; and
executing weighted calculation conforming to a weight determined for each of a plurality of gazes estimated by the plurality of estimators, and determined depending on the second condition information associated with the one estimator and the first condition information; wherein the weight is determined based on an overlap ratio at which ranges of gazes overlap.

7. A non-transitory computer-readable program recording medium recording a program which causes a computer to execute:
processing of estimating a gaze of a face included in a face image with a plurality of estimators; and
processing of determining a gaze of the face, based on first condition information including a condition relating to capture of the face image, a plurality of pieces of second condition information each including the condition associated with one estimator the plurality of estimators, and the estimated plurality of gazes, wherein the condition includes a range of the gaze to be estimated; and
processing of executing weighted calculation conforming to a weight determined for each of a plurality of gazes estimated by the plurality of estimators, and determined depending on the second condition information associated with the one estimator and the first condition informations; wherein the weight is determined based on an overlap ratio at which ranges of gazes overlap.

8. The gaze estimation device according to claim 1, wherein the plurality of estimators learn based on face images that are different in the condition from one another.

* * * * *